United States Patent [19]

Berenson et al.

[11] Patent Number: 5,225,353
[45] Date of Patent: * Jul. 6, 1993

[54] METHOD FOR IMMUNOSELECTION OF CELLS USING AVIDIN AND BIOTIN

[75] Inventors: Ronald J. Berenson, Bellevue; William I. Bensinger, Seattle, both of Wash.

[73] Assignee: Fred Hutchinson Cancer Research Center, Seattle, Wash.

[*] Notice: The portion of the term of this patent subsequent to Jun. 1, 2010 has been disclaimed.

[21] Appl. No.: 769,530

[22] Filed: Oct. 3, 1991

Related U.S. Application Data

[63] Continuation of Ser. No. 631,765, Dec. 21, 1990, abandoned, which is a continuation of Ser. No. 111,530, Jan. 27, 1987, abandoned, which is a continuation-in-part of Ser. No. 824,178, Jan. 30, 1986, abandoned.

[51] Int. Cl.$^5$ .............. C12N 13/00; C12N 5/00; A61K 35/14; G01N 33/538
[52] U.S. Cl. ..................... 436/541; 435/2; 435/172.2; 435/177; 435/240.1; 436/501; 436/530; 530/388.7; 530/388.73
[58] Field of Search .............. 435/2, 172.2, 177, 240.1; 436/501, 538, 541; 530/388.7, 388.73

[56] References Cited

U.S. PATENT DOCUMENTS

| | | | |
|---|---|---|---|
| 4,192,748 | 3/1980 | Hyden | 210/87 |
| 4,228,237 | 10/1980 | Hevey et al. | |
| 4,253,996 | 3/1981 | Katz | |
| 4,276,206 | 6/1981 | Katz | |
| 4,298,685 | 10/1981 | Parikh et al. | |
| 4,468,470 | 8/1984 | Aalberse | |
| 4,496,654 | 1/1985 | Katz et al. | |
| 4,512,763 | 4/1985 | Schneider | 604/5 |
| 4,684,609 | 8/1987 | Hsu | 435/7 |

FOREIGN PATENT DOCUMENTS 0179007 10/1985 France .

OTHER PUBLICATIONS

Berenson, R. J. et al., "Cellular Immunoabsorpton Using Monoclonal Antibodies," *Transplantation* 38(2), 136–143, 1984.

Berenson, R. J. et al., "Antigen CD34+ Marrow Cells Engraft Lethally Irradiated Baboons," *J. Clin. Invest.* 81, 951–955, 1988.

Lewis et al., "Separation of T and B cells using plastic surface coated with anti-immunoglobulin antibodies," Selected Methods in *Cellular Immunology*, Mishell et al., editors, W. H. Freeman and Co., pp. 227–234, 1980.

Edelman, "Nonenzymatic Dissociations," *Tissue Culture*, Kruse et al., editors, Academic Press, pp. 29–36, 1973.

Bayer, E. A. t al., "The avidin–biotin complex as a tool in molecular biology," TIBS, pp. N257–N259, Nov. 1978.

Chibata, I. and Wingard, L, B. Jr., (Eds.), "Immobilized Microbial Cells," *Applied Biochemistry and Bioengineering*, Wingard, L. B., Jr. et al., (Eds.), Academic Press, (vol. 4) pp. 311–349, 1983.

(List continued on next page.)

*Primary Examiner*—David L. Lacey
*Assistant Examiner*—Donald E. Adams
*Attorney, Agent, or Firm*—Christensen, O'Connor, Johnson & Kindness

[57] ABSTRACT

The selectivity of immunoselection systems employing insolubilized avidin and biotinylated specific antibody is amplified, and nonspecific recovery is improved, by employing an indirect sandwich technique using a biotin-conjugated antispecies immunoglobulin that is directed to one or more nonbiotinylated specific antibodies in conjunction with insolubilized avidin. Specific cell populations can be removed and recovered from bone marrow, providing excellent recovery of bone marrow and preservation of hematopoietic stem cells for transplantation. Mixed populations of T cells or of tumor cells can be conveniently and simultaneously removed with minimal manipulation of the marrow cells. An improved positive immunoselection method provides viable and functional recovered cells, e.g., hematopoietic stem cells or activated killer cells, that can be clinically employed.

2 Claims, 9 Drawing Sheets

OTHER PUBLICATIONS

Berenson, R. J. et al., "Hematopoietic Stem Cell Transplants," *Recent Advances in Leukemia and Lymphoma,* pp. 527–523, 1987.

Berenson, R. et al., "Transplantation of CD34+ Marrow Stem Cells in Patients with Metastatic Breast Cancer," J. Cell Biochem: Abstracts, 17th Annual Meetings, abstract K401, p. 116, 1988.

Berenson, R. J., "Selective removal of T-cells and CALLA+ lymphoblasts from human bone marrow mononuclear cells using cellular immunoabsorption with monoclonal antibodies," Abstract #C-1052 for ASCO Annual Meeting, Toronto, Canada, May 6–8, 1984.

Berman, J. W. and Basch, R. S., "Amplification of Biotin-Avidin Immunofluorescence Technique," *J. Immun. Methods* 36, pp. 335–338, 1980.

Jasiewicz, M. L. et al., "Selective Retrieval of Biotin-Labeled Cells Using Immobilized Avidin," *Exp. Cell Res.* 100, 213–217, 1976.

Prud'homme, F. J. et al., "Immune dysfunction in diabetes-prone BB rats," *J. Exp. Med.* 159: 463–478, 1984.

Basch, R. S. et al., "Cell Separation Using Positive Immunoselective Techniques," *Journal of Immunological Methods* 56, pp. 269–280, 1983.

Wormmeester, J. et al., "A Simple Method for Immunoselective Cell Separation with the Avidin-Biotin System Separation with the Avidin-Biotin System," *Journal of Immunological Methods* 67, 389–394, 1984.

International Search Report dated May 26, 1987 for counterpart International Application No. PCT/US87/00101, filed Jan. 27, 1987.

Berenson, R. J. et al., "Positive selection of viable cell populations using avidin-biotin immunoadsorption," *Journal of Immunological Methods* 91, 11–19, 1986.

Hofmann, K. et al., "Avidin-biotin affinity columns: general method for attaching biotin to peptides and proteins," *J. Am. Chem. Soc.* 100(11), 3585–3590, 1978.

Wormmeester, J. et al., "A simple method for immunoselective cell separation with the avidin-biotin system," *Biological Abstracts* 78(3): No. 19564, 1984.

Berenson, R. J. et al., "Elimination of Daudi lymphoblasts from human bone marrow using avidin-biotin immunoadsorption," *Blood* 67(2), 509–515, 1986.

Berenson R. J. et al., "In vivo reconstitution of hematopoiesis in baboons using 12.8-positive marrow cells isolated by avidin-biotin immunoadsorption," Abstract for The American Society of Hematology 28th Annual Meeting, Dec. 6–9, 1986.

Hirn-Scavennec, J. et al., "Elimination of malignant clonogenic cells from human bone marrow using floating beads coated with monoclonal antibodies," *Bone Marrow Transplantation* 1 (suppl. 1), 266–267, 1986.

Ven Katasubramanian et al, "Chemical Engineering Analysis of Immobilized Cell Systems," *Immobilized Microbial Cells,* vol. 4, 311–349, 1983.

Vector Laboratories, Inc. Catalog pp. 1–16, 1980.

Fig. 5. ENRICHMENT FOR 7.2-POSITIVE DOG BMMC

Avidin-Biotin Immunoadsorption
DT2 POSITIVE SELECTION FROM DOG PBMC

METHOD FOR IMMUNOSELECTION OF CELLS USING AVIDIN AND BIOTIN

This application is a continuation application based on prior copending application Ser. No. 07/631,765, filed on Dec. 21, 1990, now abandoned of Ronald J. Berenson and William I. Bensinger for IMMUNOSELECTION METHOD, which in turn is a continuation of application Ser. No. 07/111,530, filed on Jan. 27, 1987, abandoned, which in turn is a continuation-in-part of application Ser. No. 06/824,178, file Jan. 30, 1986, abandoned.

TECHNICAL FIELD

This invention relates to methods of immunoselection employing avidin-biotin.

BACKGROUND OF THE INVENTION

Immunoselection is a generic term that encompasses a variety of techniques in which the specificity of a selection system is conferred by an antibody or an antibody-like molecule such as a lectin or hapten. An example of such specificity is the affinity of an antibody for a specific cell surface antigen. Two general types of immunoselection techniques are practiced. Negative immunoselection involves the elimination of a specific subpopulation of components from a heterogeneous population such as a suspension of various cell types. Exclusively negative selection techniques have an inherent disadvantage: Although specific component types can be removed, the remaining components are an enriched but not a pure population. In contrast, positive immunoselection refers to the direct selection and recovery of a specific component, such as cells which express a given specificity from among a heterogeneous group of contaminating cell types. Rather than eliminating the undesired elements, positive immunoselection techniques can lead directly to the selective enrichment and even purification of targeted antigen-bearing cells. Another difference between the two techniques is that viable, functional cells are typically the desired end product of positive immunoselection techniques, while the continuing viability of negatively selected cells is usually not required.

Bone marrow transplantation provides an illustrative example of a clinical application in which immunoselection techniques have shown promise. Bone marrow transplantation is being utilized for treatment of increasing numbers of patients with hematological malignancies, aplastic anemia, solid tumors, certain congenital hematological disorders, and immunodeficiency states. The basic aim of the bone marrow transplantation treatment is to replace a defective component of the blood or immune system by first destroying the defective cells in the patient (recipient) and then transplanting omnipotential, hematopoietic stem cells derived from either the recipient (autologous transplant) or another donor (allogeneic transplant). The transplanted hemato-poietic stem cells can potentially differentiate into normal cell types that will replace the defective cells. Unfortunately, about seventy percent of patients with aplastic anemia and even fewer with leukemia survive more than one year following the bone marrow transplantation procedure. The major obstacles that limit the success of this procedure include graft-versus-host disease in patients given allogeneic transplants, and relapse possibly caused by the presence of residual tumor cells following autologous marrow transplants.

Investigators have demonstrated that graft-versus-host disease can be prevented in animals by removing T cells from the donor marrow before transplantation into the recipient. Similarly, successful autologous marrow transplants have been performed in animals in which tumor cells were first removed in vitro from the donor marrow before transplantation into the recipient. The successes of such animal studies have stimulated the development of various in vitro methods designed to eliminate T cells or tumor cells from human bone marrow. These methods have included the use of antibodies with complement, antibody-toxin conjugates, various physical separation or fractionation procedures, chemotherapeutic agents, and magnetic immunoselection. Another approach has been to use a chromatography column made of gel substrate to which monoclonal antibodies directed against T cells or tumor cells are directly linked. Transplantation 38:136, 1984; Proceedings, American Society of Clinical Oncology, Toronto 3:269 (Abstract #C-1052), 1984. Such a negative immunoselection technique avoids the toxicity to hematopoietic stem cells and decreased recovery of bone marrow that characterize some of the other in vitro techniques. However, the large quantities of monoclonal antibodies required for direct attachment to the gel (5 mg/ml) has made scale up of that procedure for clinical application to human bone marrow transplantation impractical.

The high binding efficiency between avidin and biotin has also been applied in prior immunoselection techniques. Biotin is a vitamin present in minute amounts in every living cell. Avidin is a glycoprotein isolated from raw egg white. Biotin selectively combines with avidin with a remarkably high affinity constant ($K_m = 10^{-15}M$). The avidin-biotin complex has been used as a tool in molecular biology for the following objectives: isolation of biotinderivatized materials by affinity chromatography; affinity labeling and identification studies; affinity cytochemical labeling for localization studies in fluorescence and electron microscopy; inhibition of bacteriophage; and study of cell surface molecular interactions. Bayer and .Wilcheck, TIBS, N257-N259, November 1978. With regard to the isolation of biotin-derivatized materials by affinity chromatography, biotinized rat thymocytes were reportedly retrieved using avidin which was covalently coupled to nylon meshes; no attempts were made to remove the cells from the avidin. Exp. Cell Res. 100:213-217, 1976. T-cells were reportedly depleted by treating spleen cells with biotin-conjugated antibody directed to T-cell antigen, followed by panning twice on avidin-coated plates. J. Exp. Med. 159:463-478, 1984. Another negative immunoselection technique employing avidin-biotin is described in U.S. Pat. No. 4,298,685.

Biotinylated antibodies have been used to label cells which were then removed by passing them over immobilized avidin, but unfortunately the binding between avidin and biotin has proved to be essentially irreversible. In order to use this technique for positive immunoselection, antibodies have been conjugated with biotin analogs that reportedly have the advantage that they adhere to avidin containing matrices but can be displaced by washing with authentic biotin. J. Immunol. Meth. 56:269-280, 1983.

Biotinylated antibodies and avidin-coupled sheep erythrocytes were used for rosette formation, followed by separating rosetting cells from nonrosetting cells on a density gradient. This method was reported to present the possibility of obtaining both positive and negative subpopulations with high yield. J. Immunol. Meth. 67:389–394, 1984. However, recovered cells are coated with sheep erythrocytes which could potentially affect the function of the rosetted cell population.

U.S. Pat. Nos. 4,253,996 and 4,276,206 note that the application of insolubilized avidin in the affinity chromatographic isolation of biotincontaining molecules has been limited due to the problem in recovery since the affinity of avidin to biotin is so high. Both patents reportedly circumvent this problem by preparing avidin-Sepharose conjugates with reduced affinity for biotin and thereby reportedly provide an operable positive selection technique using the avidin-biotin system.

Uses of a second, anti-species antibody in conjunction with immunoassays employing avidin and biotin are disclosed in U.S. Pat. Nos. 4,228,237, 4,468,470, and 4,496,654.

It would be advantageous to provide an improved negative immunoselection method whereby specific subpopulations of cells such as T cells and/or tumor cells could be removed from heterogeneous cell populations such as bone marrow cells with a high degree of selectivity and with a low nonspecificity, using relatively small amounts of antibody and minimal manipulation of the nonselected cells. It would also be desirable to provide an improved positive immunoselection system.

SUMMARY OF THE INVENTION

Pursuant to the invention, the selectivity of immunoselection systems employing insolubilized avidin and biotinylated specific antibody is amplified, and non-specific recovery is improved, by employing a biotin-conjugated antispecies immunoglobulin that is directed to one or more non-biotinylated specific antibodies. In an illustrative embodiment, a murine monoclonal antibody or antibody fragment is selected to bind to a specific cell subpopulation. A heterogeneous suspension of cells that includes the specific cell subpopulation is incubated with the specific murine antibody. Unbound antibody is then washed away. The cell suspension is then incubated with an antimouse immunoglobulin-biotin conjugate to form a complex of antimouse-biotin/murine antibody on the cells of the specific subpopulation. Excess antimouse-biotin is washed away. The cell suspension is then passed over a column of insolubilized avidin, to which cells of the targeted subpopulation are bound via avidin/biotin complexes. Unadsorbed cells are washed from the column. The recovery of cell populations that do not substantially react with nonbiotinylated specific antibody is amplified using this method as compared with prior techniques employing biotinylated specific antibody. Moreover, a plurality of specific antibodies, e.g., a first antibody specific for one T cell antigen and a second antibody specific for a second T cell antigen, can be simultaneously incubated with a heterogeneous cell suspension without the need to biotinylate each specific antibody. This embodiment has particular advantages for removing and recovering certain cell populations from bone marrow, providing excellent recovery of bone marrow and preservation of hematopoietic stem cells for transplantation. Mixed populations of T cells or of tumor cells can be conveniently and simultaneously removed with minimal manipulation of the marrow cells. In related applications, peripheral blood cells or tissue cell suspensions, e.g., spleen cells, can be enriched by the removal of one or more specific cell types using this method.

The invention also provides an improved positive immunoselection method: After the aforesaid unadsorbed cells are washed from the column, the remaining cells can be conveniently recovered by disassociating the antispecies/specific antibody bond (which is much weaker than the biotin/avidin bond). The recovered cells, e.g., hematopoietic stem cells or activated killer cells, can be clinically employed.

DESCRIPTION OF THE PREFERRED EMBODIMENT

Figure 1:
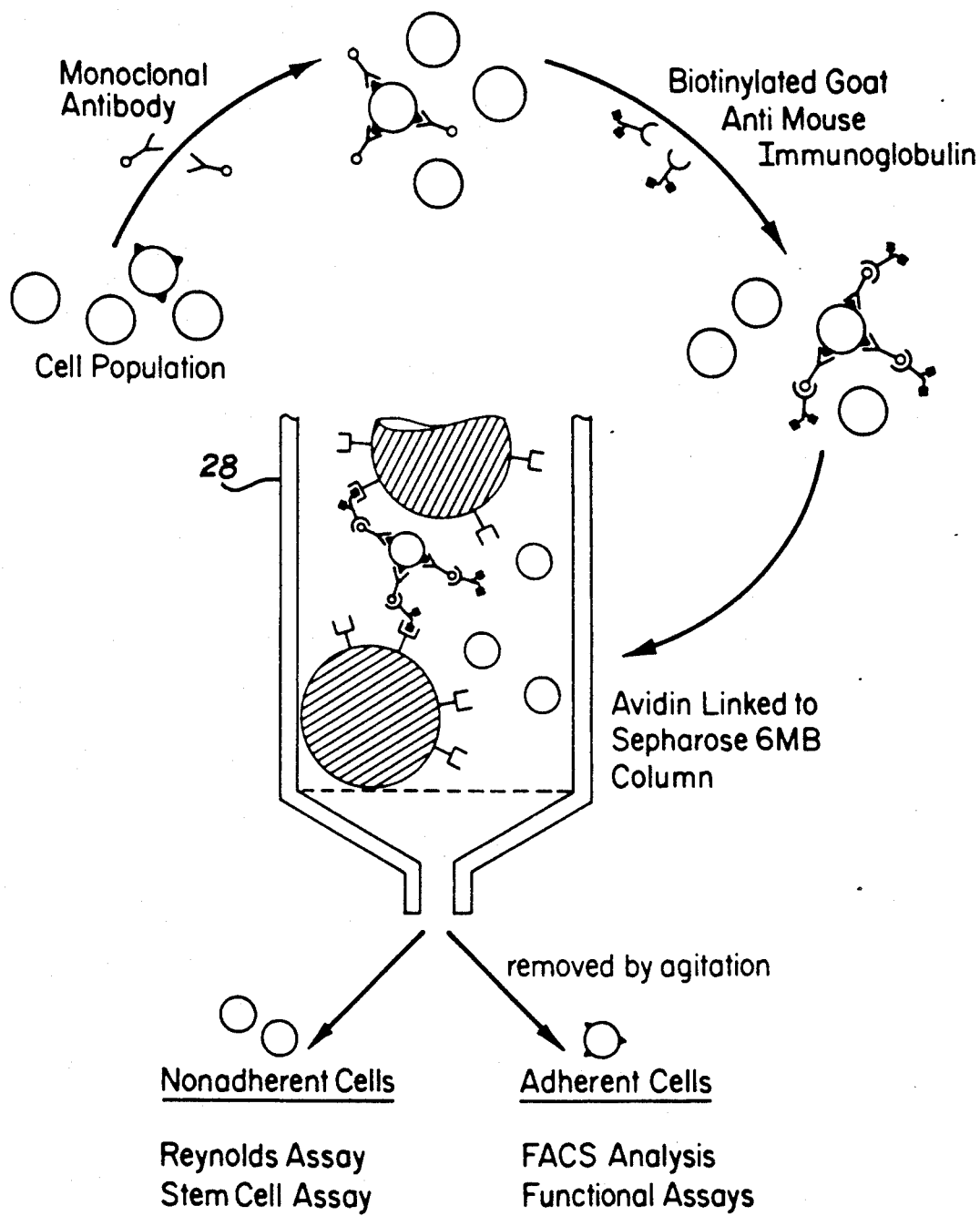
FIG. 1 is a schematic diagram of a preferred embodiment of the immunoselection method of the present invention, showing both positive and negative immunoselection techniques.

Pursuant to the invention, the selectivity of selection systems employing insolubilized avidin and biotinylated reagents is amplified, and non-specific recovery is improved, by the use of an indirect sandwich technique. In one embodiment an improved negative selection system is provided. A suspension such as a cell suspension containing one or more targeted components whose removal is desired is reacted with nonbiotinylated first reagent(s) having binding specificity for the targeted component(s). A targeted component can be, for example, a particular cell subpopulation, and the first reagent a monoclonal antibody or antibody fragment directed to antigens on the particular cells. The suspension can contain cells of bone marrow, blood, lymph node, spleen, liver, or other tissues and organs. The suspension and the first reagent are incubated to promote the formation of complexes between the first reagent and the targeted component, or first reagent/component complexes. Unreacted first reagent is preferably then removed by, e.g., a washing step. The suspension containing the first reagent/component complexes is next reacted with a biotinylated second reagent, selected because it has specificity for the first reagent, in order to associate or bind the first and second reagents and thereby form biotinylated second reagent/first reagent/component complexes. In a preferred embodiment, first reagent is a murine monoclonal antibody, and second reagent is a biotinylated anti-mouse immunoglobulin. Unreacted biotinylated second reagent may then be removed. The suspension containing the biotinylated second reagent/first reagent/component complexes is next reacted with insolubilized avidin in order to associate or bind the avidin to the biotin and thereby form insolubilized avidin/biotinylated second reagent/first reagent/component complexes. The insolubilized avidin can take the form of an avidin-coated gel that is packed inside a chromatography column. Then the remainder of the suspension is separated from the insolubilized avidin complex, thereby removing the targeted component by virtue of its incorporation into insolubilized avidin/biotinylated second reagent/first reagent/component complexes. The resulting suspension can be employed in bone marrow and other transplants.

The solid support for the insolubilized avidin can take various forms, including fibers, mesh, or tubing, and can be housed in other flow-through devices such as extracorporeal cartridges in systems for continuously removing selected components from a patient's bloodstream. Solid supports for the insolubilized avidin can also take the form of magnetic beads such as those disclosed in Reynolds, C. P., et al., Transplantation Proceedings XVII(1):434–436, February 1985, hereby incorporated by reference.

An improved immunoselection technique is provided by dissociating and recovering the targeted component from the insolubilized avidin. Adherent target cells can be conveniently dissociated by agitating the insoluble matrix to which they are bound. In other embodiments the first and second reagents in the separated insolubilized avidin/biotinylated second reagent/first reagent component complexes are selectively dissociated using available chemical techniques. For example, dithiothreitol (DTT) can be employed to dissociate disulfide bridges such as occur in large IgM antibodies and thereby effectively dissolve either or both of the antibody reagents to release the target cells from the column while nonspecifically bound adherent cells remain on the gel. Alternatively, linkages that are specifically cleavable by enzymatic or chemical agents can be inserted between the biotin molecule and the second reagent. Examples of such linkages include peptide bonds cleavable by various peptidases, disaccharide linkages cleavable by disaccharidases, or chemical bonds that can be selectively broken under mild reducing, oxidizing, acidic, or basic conditions.

Also provided are clinical kits for removing a specific cell population from a heterogeneous cell suspension. The kits typically contain insolubilized avidin in a presterilized column or cartridge housing, one or more first reagents directed to the specific cell population, and a biotinylated second reagent directed against the first reagent(s). Clinical kits providing avidin bound to magnetic beads are also provided for practicing the invention.

Figure 8:
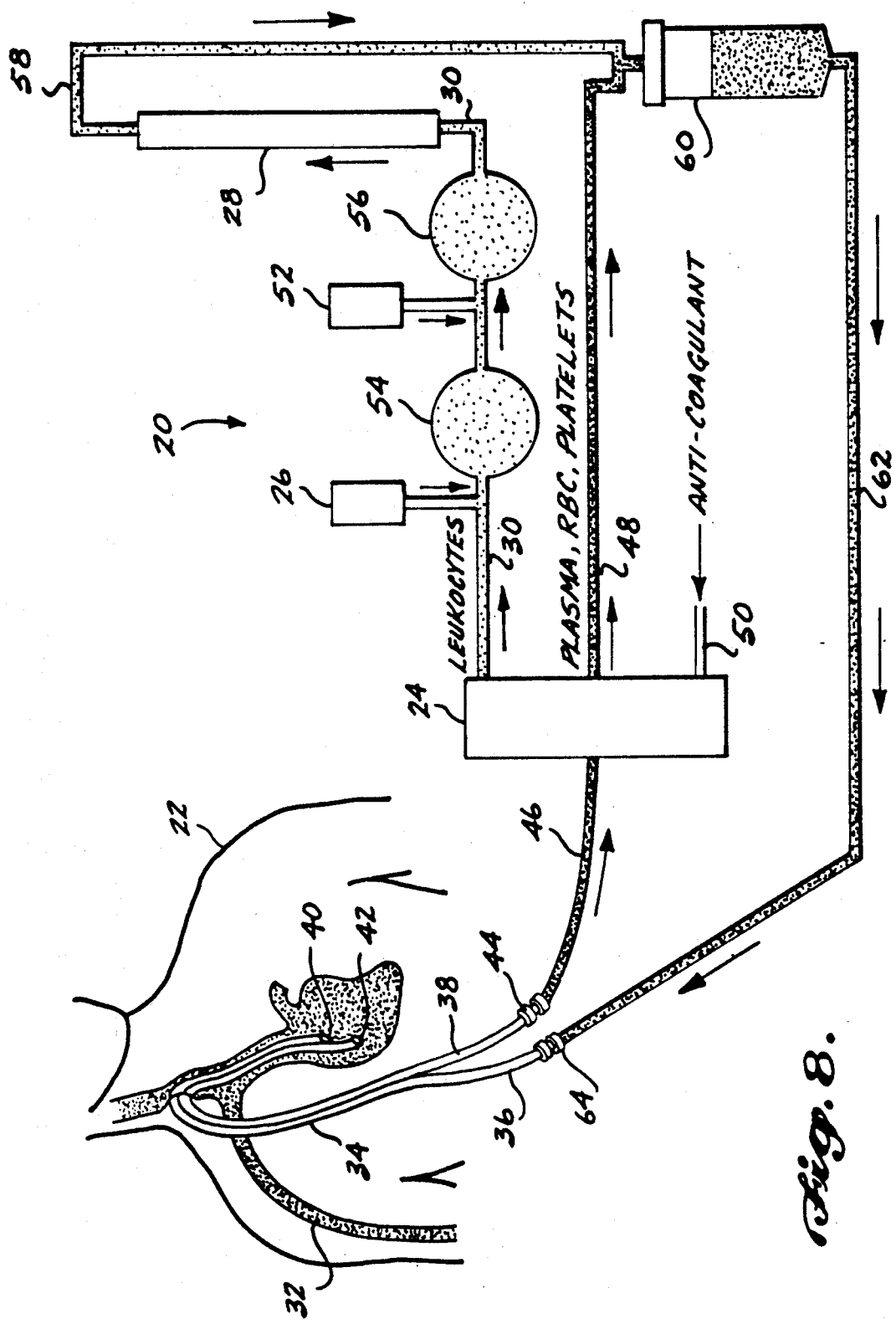
FIG. 8 is a schematic diagram of an on-line or off-line immunoselection system for removing selected components from a patient's bloodstream; and, FIG. 9 is a schematic cross section through an extracorporeal cartridge that can serve as a dialyzer, cell collector, and bioreactor.

FIG. 8 illustrates a system 20 for treating a patient 22 so as to remove specific cell populations such as immunoregulatory cells or tumor cells from the patient's blood. System 20 includes a cell centrifuge 24, at least one reagent-dispensing reservoir 26, an avidinized column 28, and, typically, a tube or conduit 30 for establishing fluid communication between these other system components 20. In the illustrated embodiment, which is suitable for continuous or intermittent on-line use, fluid connection is made between system 20 and the patient's circulating system 32 via a double-lumen central venus catheter 34. Of course, other known means of blood access, such as arteriovenous shunts, fistulas, or double venipuncture, may be similarly employed. Catheter 34 includes inlet conduit 36 and outlet conduit 38 whose respective ends 40 and 42 are adapted for insertion into the circulatory system 32 of the human or animal patient 22. Outlet conduit 38 of catheter 34 is coupled by connector 44 to tube 46 such that whole blood from patient 22 flows from outlet conduit 38, through tube 46, and into cell centrifuge 24.

Cell centrifuge 24 may be any suitable device for separating the plasma and cellular components of whole blood such that the nucleated cell fraction of blood, the so-called buffy coat layer, that is enriched with white blood cells of all types, generally termed leukocytes herein, can be isolated and delivered into tube 30. The remaining blood constituents, including substantially all of the erythrocytes (red blood cells, RBC) and platelets, and most of the plasma, flow out of the cell centrifuge 24 into tube 48. A suitable anticoagulant, such as heparin, is provided to the cell centrifuge through inlet 50 to prevent clotting.

Cell centrifuge 24 may process a continuous flow of blood received from tube 46 and deliver continuous flows of heterogeneous leukocytes and other blood constituents into tubes 30 and 48, respectively. Alternatively, an intermittent flow centrifuge 24 may be employed to collect the buffer coat layer from one unit or other preselected volume of the patient's blood at a time. Of course, the disclosed system 20 is also suitable for off-line use, as establishing direct fluid communication between the patient's bloodstream 32 and centrifuge 24 is not a prerequisite for practicing the invention. Thus, the selection of an appropriate treatment protocol can be prescribed by the attending physician on the basis of the patient's physical condition and the equipment and other facilities available at the hospital or laboratory.

As described in detail below, the buffy coat fraction flows through tube 30 into avidinized column 28. As the leukocyte-containing fraction transits along tube 30, one or more reagents from one or more reagent reservoirs 26 and 52 are introduced into tube 30. Mixing and incubation of the introduced reagent(s) with the leukocytes can be facilitated by providing one or more incubation reservoirs 54 and 56 in tube 30. After further processing in avidinized column 28, the treated leukocyte fraction flows through tube 58 into drip chamber 60, which also receives, from tube 48, the plasma containing erythrocytes and platelets. The fluids from tubes 58 and 48 are allowed to mix in drip chamber 60, and the thus reconstituted blood flows out of chamber 60 through tube 62. Tube 62 is joined, in this on-line embodiment, by connector 64 to inlet conduit 36 of catheter 34. In this way the reconstituted blood in tube 62 flows back to the patient's bloodstream 32. In a typical treatment session, the equivalent of one volume of the patient's bloodstream 32 is passed through system 20.

Treatment of the patient's blood, to selectively remove a specific component subpopulation of the heterogeneous leukocyte population, occurs as the buffy coat fraction passes through tube 30 and column 28. In one representative embodiment, system 20 is provided with first and second reagent reservoirs 26 and 52. First reservoir 26, which is disposed upstream from both second reservoir 52 and column 28, dispenses into tube 30 a predetermined amount of a nonbiotinylated first reagent having binding specificity for the targeted blood component. Downstream from first reagent reservoir 26, an incubation reservoir 54 may be provided in conduit 30 to temporarily pool the buffy coat fraction and the first reagent in order to promote the formation of first reagent/component complexes. The fluid in conduit 30 is thereafter reacted with a biotinylated second reagent, having binding affinity for the first reagent, that is introduced in metered dosage from the second reagent reservoir 52. Downstream, a second incubation reservoir 56 may similarly be provided in conduit 30 in order to promote the formation of second reagent/first reagent/component complexes. Thereafter, the thus-far processed fluid is directed through column 28, which contains insolubilized avidin that selectively binds biotin and thereby removes biotinylated second reagent/first reagent/component complexes from the buffy coat fluid.

In other respresentative embodiments, only a single reagent reservoir 26 need be employed. For example, reagent reservoir 26 can deliver a mixture of the first reagent and the biotinylated second reagent into tube 30. Alternatively, reagent reservoir 26 can deliver a biotinylated first reagent into tube 30, in order to form biotinylated first reagent/component complexes that will selectively bind to the avidinized surfaces in column 28.

Since any free biotinylated second (or first) reagent can also bind to the avidinized sites in column 28, the efficiency of column 28 can be enhanced by promoting complete association of the biotinylated reagent with the targeted component during the transit through conduit 30. Thus, the avidin sites in column 28 will be efficiently used to productively remove only biotinylated component complexes from the column. One way of approaching this objective is to provide one or more incubation chambers 54 and 56 in conduit 30, as discussed above. Also, inflow of the first and second reagents from reservoirs 26 and 52 can be metered in order to insure that one or both of the reagent concentrations are below the saturation concentration of the targeted leukocyte subpopulation in the patient's buffy coat fraction. In addition, the downstream incubation reservoir 56 can take the form of a dialyzer device having a membrane with pores sized to permit and promote passage of free biotinylated antibody, but not cellular constituents, out of conduit 30 for disposal.

Column 28, as discussed above, can take the form of a sterilized chromatography column or cartridge housing containing an inert support to which avidin has been insolubilized. The inert support may be silica, glass, plastic, or any other nonreactive or nondegradable material, and may be in the shape of beads or in other suitable shapes. Fluid flow through column 28 may be ascending, as shown here, or descending, and may be driven by a pumping mechanism, which may be incorporated into centrifuge 24, or by gravity flow, particularly for off-line applications.

Figure 9:
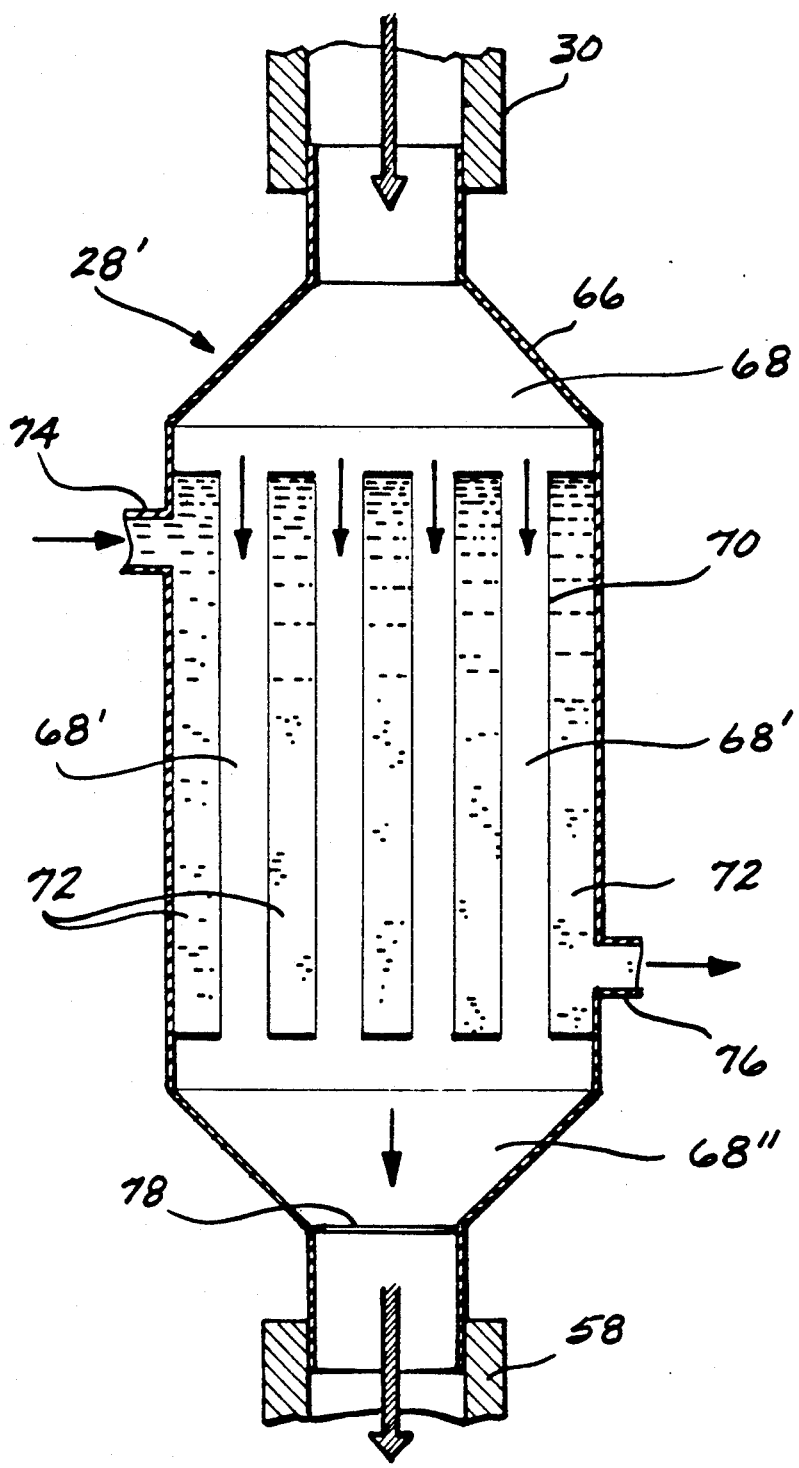

FIG. 9 shows an embodiment of avidinized column 28' that is based upon available hollow fiber technology. The cartridge housing 66, made of an inert material such as plastic, is configured so that a fluid flow path 68 can be established between tubes 30 and 58 in system 20. At least a portion of flow path 68 is made up of semipermeable tubing 70 that, like a dialysis membrane, is selectively porous such that antibodies, but not cells, can diffuse through tubing 70 into a surrounding reservoir 72. For use in the subject immunoselection process, reservoir 72 contains water or preferably a saline solution at a concentration selected to simultaneously promote the selective diffusion of free biotinylated reagent and yet avoid osmotic shock to the cells that remain in flow path 68'. Reservoir 72 may be closed or, as shown here, provided with an inflow port 74 and an outflow port 76, so that the dialysate or other fluid in reservoir 72 can be continuously or periodically replenished. The semipermeable hollow fibers 70 are typically disposed in parallel array within cartridge 28' so as to maximize contact of the biotinylated buffy coat fraction from tube 30 with the semipermeable membrane 70 that is in intimate contact with the dialysate in reservoir 72. The provision of avidinized surfaces in cartridge 28 can follow several strategies, depending upon usage. In one embodiment, avidin is insolubilized on the inner walls of dialysis tubing 70, that is, on the porous surfaces in contact with fluid flow path 68'. In another embodiment, avidin-coated surfaces, such as beads, fibrous meshworks, or the like (not shown), are provided in the flow path 68" downstream from the semipermeable membranes 70. The latter embodiment is considered preferred for the purpose of removing free biotinylated reagent prior to contacting the cellular fraction with the insolubilized avidin. If avidin-coated beads are housed within cartridge 28', a stainless steel screen 78, sized to permit passage of cells, but not the beads, can be provided in the flow path 68 downstream from wherever the beads are sequestered.

In another embodiment, cartridge 28' is not provided with any avidinized surfaces and is employed simply as a dialyzer to remove free biotinylated reagent prior to contacting the buffy coat fraction with an avidinized column 20. As such, this embodiment of cartridge 28' could replace incubation reservoir 56 in system 20. In order to substantially inhibit back diffusion of free biotinylated reagent from reservoir 72 into flow path 68', the outside surfaces of the dialysis tubing 70 may be avidinized. Alternatively, reservoir 72 may be packed with avidin-coated beads. It is further contemplated that the two foregoing embodiments of cartridge 28' can be coupled in series in system 20, with the one containing avidinized surfaces in flow path 68 being disposed downstream from the other, which serves only as a dialyzer. For convenience, the foregoing dialyzing and cell collecting embodiments can also be manufactured within a single housing 66.

In the subject immunoselection process, a cartridge 28' containing avidinized surfaces in flow path 68 can be used to selectively remove biotinylated component complexes from the heterogeneous leukocyte fraction of mammalian blood. For example, tumor cells can be thereby selectively removed from the bloodstream of patients with abnormally high leukocyte titers, as in certain leukemias, after which treatment cartridge 28' containing bound tumor cells will typically be immediately disposed. Cartridge 28' can also be employed for positive immunoselection. For example, after the targeted leukocyte subpopulation becomes bound, by virtue of the disclosed biotinylated reagent(s), to the avidinized surfaces in flow path 68, cartridge 28' is removed from system 20' and the bound cells recovered. Physiological saline solution is first run through flow path 68, to rinse any unbound material from cartridge 28'. Then the flow rate of the rinsing solution can be increased, by some ten to twenty times, in order to dissociate the targeted cells from the insolubilized avidin.

In many cases, expansion of such positively selected cell populations will be desirable prior to reinfusion into the patient. Cartridge 28' is eminently suited to serve as a bioreactor for this purpose as well. For service as a bioreactor, the avidinized surfaces should be located within the semipermeable fibers 70, within flow paths 68'. After serving to selectively remove the targeted cell population, e.g., immature lymphocytes, from the patient's blood, cartridge 28' is removed from system 20 in order to expand the population of harvested cells in situ. For this purpose, a nutrient fluid containing a growth factor, such as an interleukin, is circulated through flow path 68 and/or reservoir 72 in order to promote mitosis, differentiation or activation of the harvested cells into what in many cases will be more mature cells, e.g., cytotoxic killer cells, that can be used for therapeutic purposes. After suitable expansion, the bound cells and any progeny cells are flushed from cartridge 28' for reinfusion into the patient. As an auxiliary step in any of the disclosed positive selection strategies, the harvested cells can be subjected to one or more additional immunoselection passages, using the same or another first reagent, in order to assure the homogeneity of the selected cells.

Such positively selected cells can serve many therapeutic purposes. Immature populations of peripheral lymphocytes can be collected for in vitro exposure to growth factors suitable to direct their maturation and expand their population prior to autologous reinfusion into the patient. For example, lymphocyte activated killer cells (LAK) can be raised in this manner for cancer therapy. Killer cells have also been suggested for AIDS therapies. Other components of cellular immunity can be similarly isolated and enlisted, for example, certain suppressor lymphocytes for treating thyroid diseases, T4 lymphocytes for treating AIDS, certain subpopulations of lymphocytes for multiple sclerosis, and certain macrophages for attacking the chloresterol plaques associated with atherosclerosis. From bone marrow, hematopoietic stem cells can be selectively recovered for treating cancer, hematological disorders, or genetic diseases by gene therapy. For example, once collected in cartridge 28', the stem cells can be exposed in situ to off-line percolation of viral or other vectors for gene transfer and subsequent selection of transfected cells.

Abnormalities in lymphocyte populations involving excessive numbers of circulating cells can be treated by negative cell selection using the subject method and equipment, either on-line or off-line. Illustrative examples include the possibility of treating rheumatoid arthritis by reducing the circulating titer of T-helper cells. Similarly, circulating viruses and parasites can be removed from blood using the subject method. Tumor cells and T cells can be removed from bone marrow.

The subject method can also be used to enhance the efficiency of monoclonal antibody production techniques. For example, peripheral blood lymphocytes can be reacted with a first reagent in the form of an anti-clonotypic antibody that mimics a tumor associated antigen, in order to isolate lymphocytes reactive to the tumor cells. The isolated lymphocyte subpopulation can be fused with transformed cells to produce hybridomas. Since the B cells are preselected using the subject method, the massive screenings of fused cells that are typically required to select appropriate hybridomas can be eliminated, with attendant potential for more directly and expeditiously customizing antibodies for particular patients. Similarly, the first reagent can be antigen, to isolate lymphocytes reactive with the antigen, in which case the second reagent can be a biotinylated antibody directed against a separate epitope on the first reagent.

In a similar manner, the first reagent can be a sterilized viral particle, in order to harvest cells specifically reactive with the virus for in vitro expansion in the presence of the antigen and interleukin-2.

The subject method can also be employed as a sensitive assay for detecting cancer remission or metastases, by monitoring for the presence of tumor cells in a patient's bloodstream or bone marrow.

Another direct application is to remove cells that may be implicated in causing or inducing tissue rejection from blood and blood constituents prior to nonautologous transfusion. For example, Class II (Ia) bearing cells can thereby be eliminated from platelet concentrations, in order to reduce or eliminate the immunogenicity of the platelets, prior to transfusion, or to provide allogeneic tissue suitable for inducing a state of tolerance in the recipient prior to the transfusion or transplantation of other tissues or organs. After incubation with the first and second reagents, e.g., mouse anti-Ia antibody and biotinylated antimouse antibody, the whole blood or platelet concentration may be passed through avidinized column 28, or simply transferred to a plastic storage bag having avidinized inner walls, for complete and selective removal of the targeted cells.

The following Examples are presented to illustrate the advantages of the present invention and to assist one of ordinary skill in making and using the same. The following Examples are not intended in any way to otherwise limit the scope of the disclosure or the protection granted by Letters Patent hereon.

EXAMPLE 1

A purified murine monoclonal IgG2a antibody (2H7) to the human B cell differentiation antigen, Bp32(CD20), was biotinylated as follows. Antibody 2H7 (Genetic Systems Corporation, Seattle, Wash.) was dialyzed in 0.1M $NaHCO_3$ and adjusted to a concentration of 1 mg/ml. N-Hydroxysuccinimidobiotin (Sigma Chemical Co., St. Louis, Mo.) was dissolved in dimethylsulfoxide (DMSO) at a concentration of 1 mg/ml. Unless otherwise specified below, 60 ul of this biotin solution were added to each ml of the antibody solution and incubated for 4 hours at room temperature. The mixture was then dialyzed in phosphate-buffered saline (PBS; 8 mM $Na_2HPO_4$, 0.15 mM $KH_2PO_4$, 0.137M NaCl, 2.7 mM KCl, pH=7.4) and stored at 4° C.

EXAMPLE 2

Avidin conjugation to solid phase substrate

Cyanogen bromide activated Sepharose 6MB (Pharmacia, Piscataway, N.J.) was swollen for 35-45 min in 1 mM HCl. The gel was washed with additional 1 mM HCl, followed by 0.1M NaHCO$_3$ in 0.5M NaCl at pH=8.3 ("coupling buffer"). Avidin (Sigma Chemical Co.) was dissolved and dialyzed in coupling buffer at a concentration of approximately 1 mg/ml and then continuously mixed with the gel for 1 hour at room temperature. The eluate fraction was collected, and the efficiency of conjugation (which always exceeded 95%) was determined by measurement of protein concentration. The concentration of avidin linked to the gel varied between 50 ug/ml and 2 mg/ml of gel. After washing the gel in an alternating fashion with 0.1M sodium acetate in 0.5M NaCl at pH=4.5 ("washing buffer") and coupling buffer, 0.2M glycine in coupling buffer was added to block unconjugated sites. After washing, the gel was stored in PBS with 0.1% sodium azide at 4° C.

EXAMPLE 3

Preparation and use of avidin-insolubilized column

The avidin-conjugated gel from Example 2 was packed in Pharmacia K9/15 columns (Pharmacia). Fifteen million treated cells (see below) were suspended in a solution (PBS/BSA) of 0.5 ml PBS with 2% bovine serum albumin (BSA). The cell suspension was continuously passed through a 3 ml column bed of the avidin-conjugated gel at a flow rate of approximately 0.5 ml/min using PBS/BSA until a total of 10 ml of eluate was collected. By trypan blue dye exclusion, cell viability was judged to be greater than 98%. To regenerate the column, the gel was extensively washed with PBS (without BSA) and mechanically agitated using a Pasteur pipette to dislodge adherent cells. The gel was then sequentially washed three times with washing buffer and coupling buffer and stored in PBS with 0.1% sodium azide at 4° C.

For certain experiments the K9/15 column including rubber stopper and tubing was sterilized with ethylene oxide. The column was then packed with the avidin-conjugated gel and allowed to incubate for 30 min with 0.05% formaldehyde (V/V) in PBS. The formaldehyde was then removed by extensive washing with PBS. No loss of immunoadsorption efficiency occurred using this method of sterilization.

EXAMPLE 4

Intracellular labeling of tumor cells

Daudi is a human lymphoblastoid B cell line originally derived from a patient with Burkitt's lymphoma. Cancer Res. 28: 1300, 1968. The Daudi cell line was maintained in our laboratory by serial passage in tissue culture medium containing RPMI 1640 with 10% fetal calf serum, sodium pyruvate, L-glutamine, streptomycin, and penicillin. Indirect immunofluorescence staining and analysis (as described in J.Exp.Med. 110: 875, 1959) using a fluorescence-activated cell sorter (FACS IV; Becton Dickinson, Mountain View, Calif.) confirmed that 100% of the Daudi cells bear surface IgM. These studies also demonstrated that all cells expressed the pan-B cell marker Bp32(CD20).

Intracellular labeling of Daudi cells with fluorescein isothiocyanate (FITC) was performed using a modification of the procedure described in J. Immunol. Methods 37: 97, 1980. Briefly, Daudi cells were incubated with 60 ug/ml FITC (Sigma Chemical Co.) in PBS for 20 min at 37° C. Cold PBS was added to stop labeling, and the cells were centrifuged through an underlayer of fetal calf serum to remove excess FITC. Cells were then washed twice with PBS. This method produced bright intracellular fluorescence in 100% of the cells. Furthermore, cell viability assessed by trypan blue exclusion was identical in FITC-labeled Daudi cells as compared to unlabeled Daudi cells. Immunofluorescence staining with rhodamine isothiocyanate-conjugated antibody 2H7 demonstrated that cell surface expression of Bp32(CD20) was unaffected by the FITC-labeling of Daudi cells.

EXAMPLE 5

Treatment of cells with biotinylated antibodies

In addition to the antibody 2H7 described in Example 1, the following antibodies were used: A purified murine monoclonal IgG2a antibody (DM1; Becton-Dickinson, Mountain View, Calif.) specifically recognizes the u heavy chain of human immunoglobulin. A monoclonal IgG2a antibody (9E8; Genetic Systems) recognizes the p(15)E antigen of murine leukemia virus and is not reactive with human tissues including bone marrow or Daudi tumor cells. Affinity purified goat antimouse immunoglobulin (GAMIg), biotinylated goat antimouse immunoglobulin (B-GAMIg), and biotinylated F(ab')$_2$ goat antimouse immunoglobulin (B-F(ab')$_2$-GAMIg) were obtained from Tago, Inc., Burlingame, Calif.

Bone marrow mononuclear cells were obtained by Ficoll-Hypaque (specific gravity=1.077; Pharmacia) density gradient centrifugation from bone marrow samples (5-10 ml) obtained from healthy donors.

Concentrations of antibodies utilized in these experiments were based on immunofluorescence staining and FACS analysis which demonstrated that a minimum of 50-100 ug/ml of unconjugated or biotinylated antibody 2H7 or 5-10 ug/ml of antibody DM1 were respectively required to saturate the binding sites for Bp32 or u on Daudi cells (data not shown).

Biotinylated Antibody 2H7

Fifteen million cells per ml of bone marrow contaminated with 5-10% Daudi cells were incubated for 30 minutes with biotinylated antibody 2H7 in PBS/BSA at 4° C. Cells were then washed twice with PBS/BSA before column treatment.

Biotinylated goat antimouse antisera

Fifteen million cells per ml of a similar bone marrow and Daudi cell mixture were incubated for 30 minutes with either antibody 2H7 or antibody DM1 is PBS/BSA at 4° C. Cells were washed twice after incubation with the monoclonal antibody before and twice again after incubation with B-GAMIg or B-F(ab')$_2$-GAMIg for 30 minutes at 4° C.

EXAMPLE 6

Detection of residual tumor cells

A known number of the bone marrow mononuclear cells admixed with a known number of the labeled Daudi cells from Example 4 were placed into 96 well flat-bottom microdilution plates (Costar, Cambridge, Mass.) and examined with a Leitz inverted fluorescence microscope. A series of preliminary experiments demonstrated that a single FITC-labeled Daudi cell could be detected in a well containing a total of one million cells, representing a tumor cell contamination of 0.0001%.

Unless otherwise specified below, aliquot samples of 1000 pretreated cells were placed in microdilution wells; after column treatment, 100,000 treated cells were placed in neighboring wells for comparison. The numbers of FITC-stained cells were counted in three pretreated and three treated wells and averaged to determine the number of tumor cells per 1000 total cells before column treatment and the number of tumor cells per 100,000 cells in the treated group, respectively. Total cell counts were performed with a hemacytometer. The Log Removal of Daudi cells was calculated from absolute cell counts: The relative percentage of FITC-labeled cells before and after column treatment, indicating the removal of tumor cells, was determined as follows:

$$\log \frac{\frac{\% \text{ labeled cells in}}{\text{pretreated sample}} \times \frac{\text{total number of cells}}{\text{in pretreated sample}}}{\frac{\% \text{ labeled cells in}}{\text{treated sample}} \times \frac{\text{total number of cells}}{\text{in treated sample}}}$$

Percentage of Recovery was determined as follows:

$$100 \frac{\frac{\% \text{ non-labeled cells}}{\text{in treated sample}} \times \frac{\text{total number of cells}}{\text{in treated sample}}}{\frac{\% \text{ non-labeled cells}}{\text{in pretreated sample}} \times \frac{\text{total number of cells}}{\text{in pretreated sample}}}$$

For example, the following calculations are from an experiment treating a mixture of bone marrow and FITC-labeled Daudi cells successively with 10 ug/ml antibody DM1 and 1: 100 dilution of B-GAMIg, and then passing the treated cells over a 3 ml column bed of Sepharose containing 1 mg/ml of avidin. The pretreatment sample had a mean of 58 FITC-labeled cells (52, 59, 62 labeled cells counted in 3 separate pretreatment wells) per 1,000 cells (or 5.8% FITC-labeled cells); while the posttreatment sample contained a mean of 21 FITC-labeled cells (19, 22, 22 labeled cells counted in 3 separate walls) per $10^5$ cells (or 0.021% FITC-labeled cells). There were a total of $15.0 \times 10^6$ cells in the pretreatment sample, and $11.4 \times 10^6$ cells in the post treatment sample.

$$\text{Log Removal} = \log \frac{(5.8\%)(15.0 \times 10^6)}{(0.021\%)(11.4 \times 10^6)} = 2.56.$$

$$\text{Percentage Recovery} = 100 \frac{(99.98\%)(11.4 \times 10^6)}{(94.2\%)(15.0 \times 10^6)} = 80.7\%.$$

EXAMPLE 7

Assay system for hematopoietic progenitors

The assay system for culturing committed granulocyte-monocyte progenitors (CFU-C) described in Exp. Hematol. 6:114, 1978, was followed. Briefly, $1.0 \times 10^5$ cells were cultured in triplicate in 1 ml aliquot mixtures containing conditioned medium from phytohaemagglutinin-(Wellcome Labs, Oxford, England) stimulated peripheral blood lymphocytes, agar (Bactoagon, Difco, Detroit, Mich.), and MEM alpha medium (Gibco, Grand Island, N.Y.). Colonies were counted after 14 days incubation at 37° C. in 5% $CO_2$ using an inverted microscope.

EXAMPLE 8

Depletion of Daudi cells with biotinylated antibody 2H7

Figure 2:
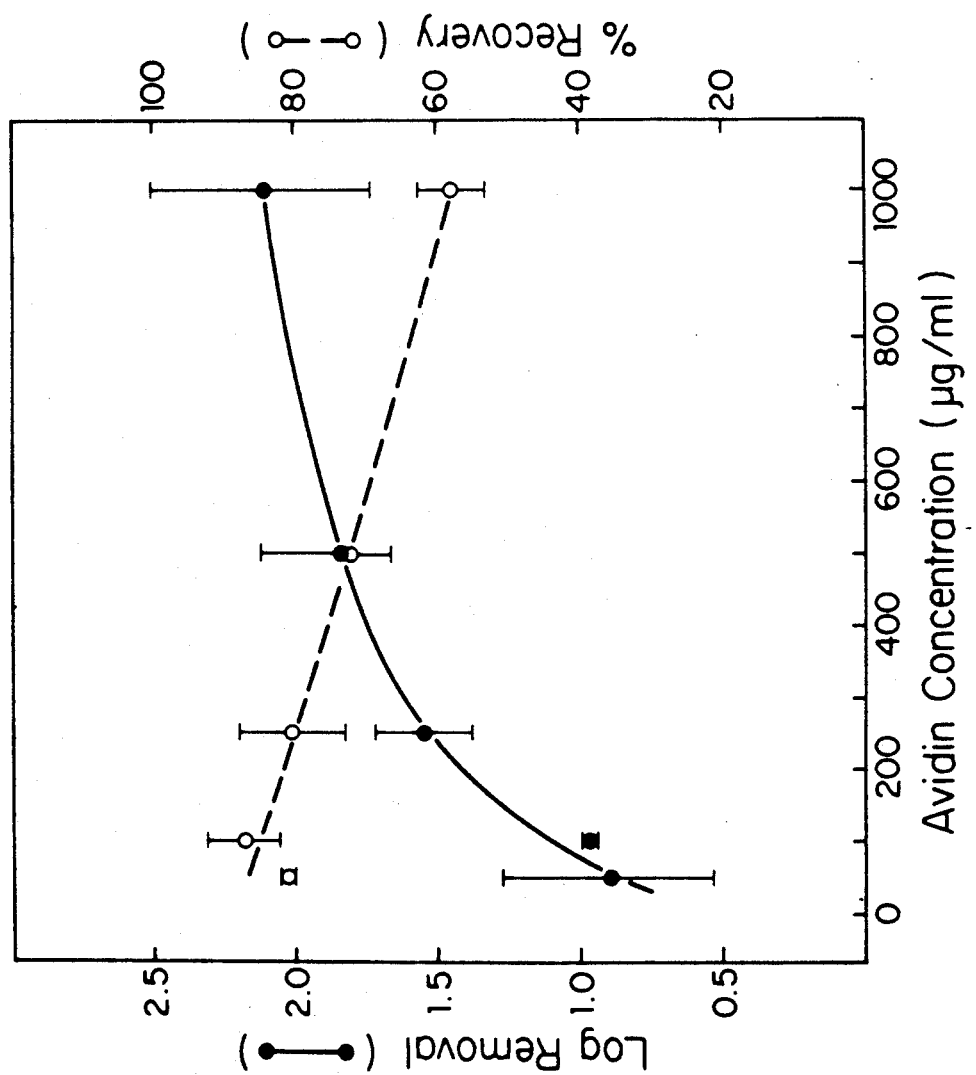
FIG. 2 is a graph showing the effect of the concentration of avidin linked to Sepharose on the log removal of Daudi cancer cells and percent recovery of noncancerous bone marrow cells after treatment with biotinylated specific antibody 2H7, as described in Example 8.

FIG. 2 summarizes the results from a series of experiments in which fifteen million bone marrow cells containing 5–10% Daudi cells were treated with 100 ug/ml biotinylated antibody 2H7 and then passed over a 3 ml column bed of Sepharose 6MB linked to the indicated amounts of avidin. Avidin concentration (ug/ml) is plotted on the abscissa. Log Removal (solid circles) and Percentage Recovery (open circles) are plotted on the ordinates. Each data point represents the results of two to four separate experiments.

FIG. 2 shows that increasing concentration of avidin on the gel was correlated with improved removal of Daudi cells. Avidin concentrations of less than or equal to 100 ug/ml resulted in less than one log depletion, while concentration of 1000 ug/ml were able to produce over two log removal of Daudi cells from bone marrow. However, increasing the concentration of avidin on the gel also caused decreased recovery of bone marrow cells.

Attempts were made to improve the recovery of bone marrow cells by decreasing the biotin/antibody conjugation ratio. Biotin/avidin conjugates were prepared by incubating antibody 2H7 (1 mg/ml) with the concentrations of N-Hydroxysuccinimidobiotin indicated in TABLE 1 for four hours. Fifteen million bone marrow cells containing 5–10% Daudi cells were incubated for 30 minutes with 100 ug/ml biotinylated antibody 2H7 and passed over 3 ml column bed of Sepharose containing 1 mg/ml avidin. TABLE 1 shows the effect of varying the degree of biotinylation of the specific antibody upon log removal of the specific targeted subpopulation and upon percentage of recovery of the remaining cells.

TABLE 1

| Concentration of Biotin Ester (ug/ml) | Log Removal | % Recovery |
| --- | --- | --- |
| 60 | 2.10 ± 40 | 57.8 ± 4.6 |
| 30 | 1.49 | 72.9 |
| 20 | 1.55 | 82.5 |
| 10 | 0.90 | 86.0 |
| 5 | 0.64 | 96.4 |
| 1 | 0.26 | 89.3 |

The results shown in TABLE 1 indicate that decreasing the biotin/antibody conjugation ratio led to increased marrow recovery, but that tumor cell removal was decreased.

In addition, using another source of avidin (Vector Laboratories, Burlingame, Calif.), altering elution fluid conditions such as pH or bovine serum albumin concentration, or incubating cells with free biotin or unconjugated antibody (to block Fc receptors) did not improve bone marrow recovery. Passage of treated cells over a column containing Sepharose linked to Strepavidin (Sigma Chemical Co.), an avidin derivative reported to have less nonspecific binding properties than avidin, did improve recovery but at the expense of less efficient removal of Daudi cells (data not shown).

EXAMPLE 9

Figure 3:
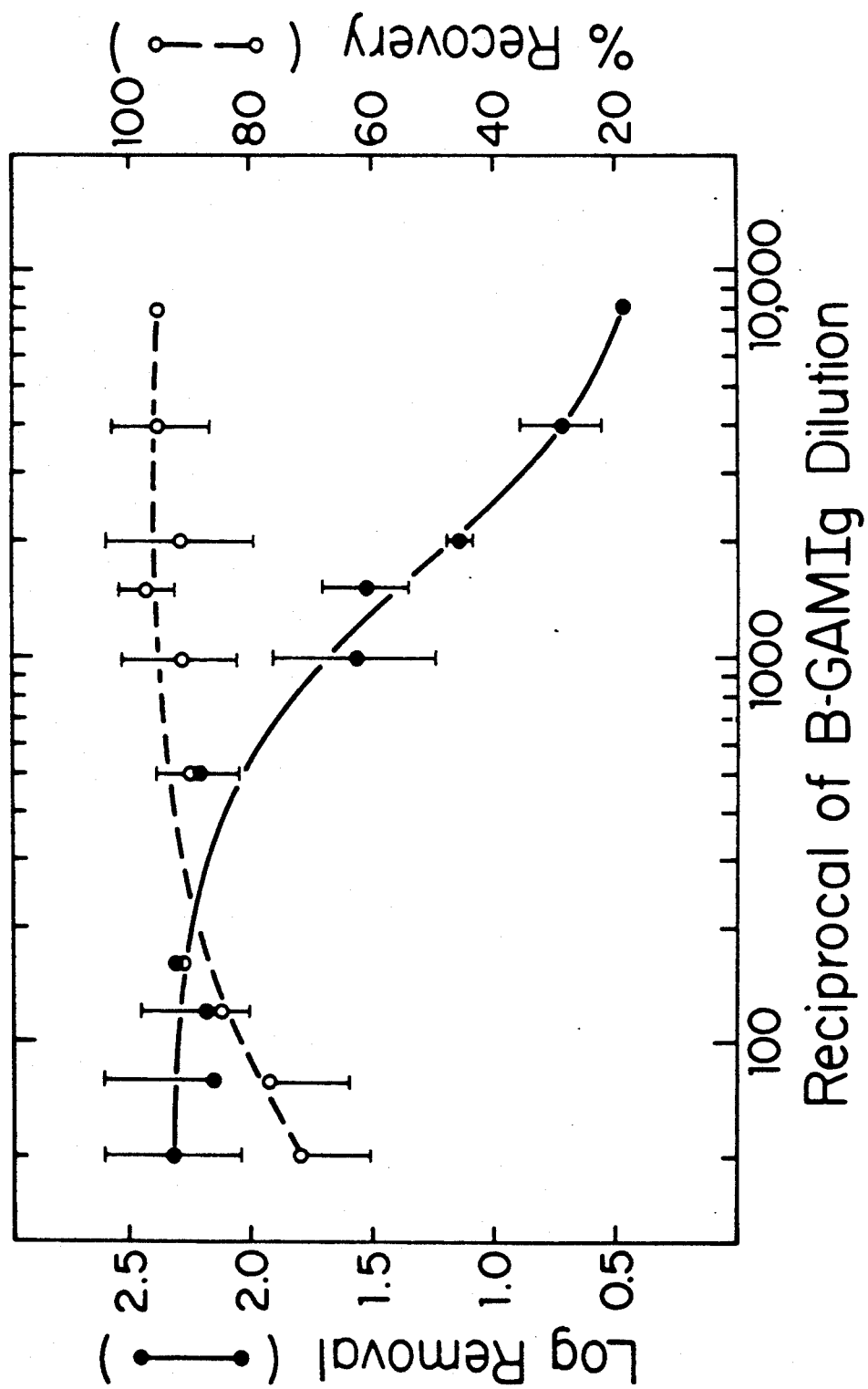
FIG. 3 is a graph showing the effect of biotinylated anti-mouse antibody B-GAMIg on log removal of Daudi cancer cells and percent recovery of noncancerous bone marrow cells after treatment with nonbiotinylated murine antibody 2H7, as described in Example 9.

Depletion of Daudi cells with antibody 2H7 followed by biotinylated goat antimouse immunoglobulin Significantly more effective removal of tumor cells from bone marrow was achieved when the cell mixture was successively treated with tumor-specific murine antibody followed by a biotinylated goat antimouse immunoglobulin and then passed over an avidinized column. Specifically, fifteen million bone marrow cells containing 5-10% Daudi cells were treated successively with 200 ug/ml antibody 2H7 and various dilutions of B-GAMIg and then passed over a 3 ml column bed of Sepharose containing 1.0 mg/ml avidin. Referring to FIG. 3, more than two logs of Daudi cells were removed when dilutions of B-GAMIg ranging from 1:50 to 1:500 were used, and more than one log of Daudi cells could be eliminated with dilutions as high as 1:2000. Marrow recovery improved as the dilution was increased from 1:50 to 1:120 and then remained constant at greater than 90% between dilutions of 1:160 and 1:8000. Each data point (except 1:160 and 1:1800) represents the results of two to eleven experiments.

Increasing the concentration of antibody 2H7 beyond saturating levels (100 ug/ml) did not improve Daudi cell removal when B-GAMIg dilution of 1:50 was utilized: 2.37±0.02 log removal at 100 ug/ml as compared with 2.31±0.28 log removal at 200 ug/ml.

Control experiments demonstrated the necessity for both a monoclonal antibody reactive with the tumor cell and a second, biotinylated antispecies antibody (data not shown). Treatment of the bone marrow and Daudi cell mixture with antibody 2H7 and nonbiotinylated GAMIg or without a second antibody did not lead to either removal of Daudi cells or loss of bone marrow. Using a monoclonal antibody nonreactive with Daudi cells and human bone marrow also had no effect on Daudi cell depletion. Daudi cells were not removed if treated cells were passed over a column constructed with 1 mg/ml albumin linked to Sepharose. Finally, treatment of a mixture of bone marrow and a Bp32-negative T cell line, Jurkat, with antibody 2H7 followed by B-GAMIg did not result in tumor cell removal. (Jurkat is a T cell lymphoblastic leukemia line that does not express surface IgM or Bp32 antigen. Int. J. Cancer 19:621, 1977.)

EXAMPLE 10

Depletion of Daudi cells with antibody 2H7 followed by biotinylated F(ab')2goat antimouse immunoglobulin Daudi cells were eliminated from bone marrow when treated successively with antibody 2H7 and B-F(ab')2-GAMIg and then passed over avidin-Sepharose. Specifically, fifteen million bone marrow cells containing 5-10% Daudi cells were treated successively with varying concentrations of antibody 2H7 and B-F(ab')2-GAMIg and then passed over a 3 ml column bed of Sepharose with 1 mg/ml avidin. The results are shown in TABLE 2.

TABLE 2

| 2H7 Concentration (ug/ml) | B-F(ab')2-GAMIg dilution | Log Removal | % Recovery |
|---|---|---|---|
| 200 | 1:5 | 1.83 | 72.8 |
| 100 | 1:10 | 1.82 ± .13 | 92.3 ± 10.7 |
| 200 | 1:10 | 1.92 ± .06 | 88.3 ± 12.2 |
| 50 | 1:50 | 0.76 | 100 |
| 100 | 1:50 | 1.22 | 100 |

TABLE 2-continued

| 2H7 Concentration (ug/ml) | B-F(ab')2-GAMIg dilution | Log Removal | % Recovery |
|---|---|---|---|
| 200 | 1:50 | 1.25 | 98.1 |
| 200 | 1:100 | 0.64 | 100 |

Very high concentrations of B-F(ab')2-GAMIg were required for optimal Daudi cell removal. Essentially no differences were observed in Daudi cell removal whether cells were treated with 100 or 200 ug/ml of antibody 2H7. Excellent recovery of bone marrow was observed even at a dilution of 1:10 B-F(ab')2-GAMIg, but Daudi cell depletion was decreased in these experiments compared with results using B-GAMIg.

EXAMPLE 11

Depletion of Daudi with antibody DM1 followed by B-GAMIg

Effective removal of Daudi cells and excellent recovery of bone marrow were observed when mixtures of bone marrow and Daudi cells were treated successively with murine antibody DM1 (specifically recognizing the u heavy chain of human immunoglobulin) and B-GAMIg and then passed over an avidin-Sepharose 6MB column. Little variability was observed using antibody DM1 at concentrations from 10-30 ug/ml (and a constant 1:100 dilution of B-GAMIg), with approximately 2.5 logs of Daudi cells removed and 80-85% recovery of bone marrow: 10 ug/ml=2.53±0.28 log removal, 84.0±13.8% recovery; 20 ug/ml=2.45±0.09 log removal, 79.5±6.4% recovery; 30 ug/ml=2.61±0.04 log removal, 85.4±0.3% recovery. Identical results were observed when mixtures of Daudi cells and bone marrow cells were treated in the presence or absence of 0.1% sodium azide, suggesting that antigenic modulation does not affect Daudi cell removal (data not shown).

Figure 4:
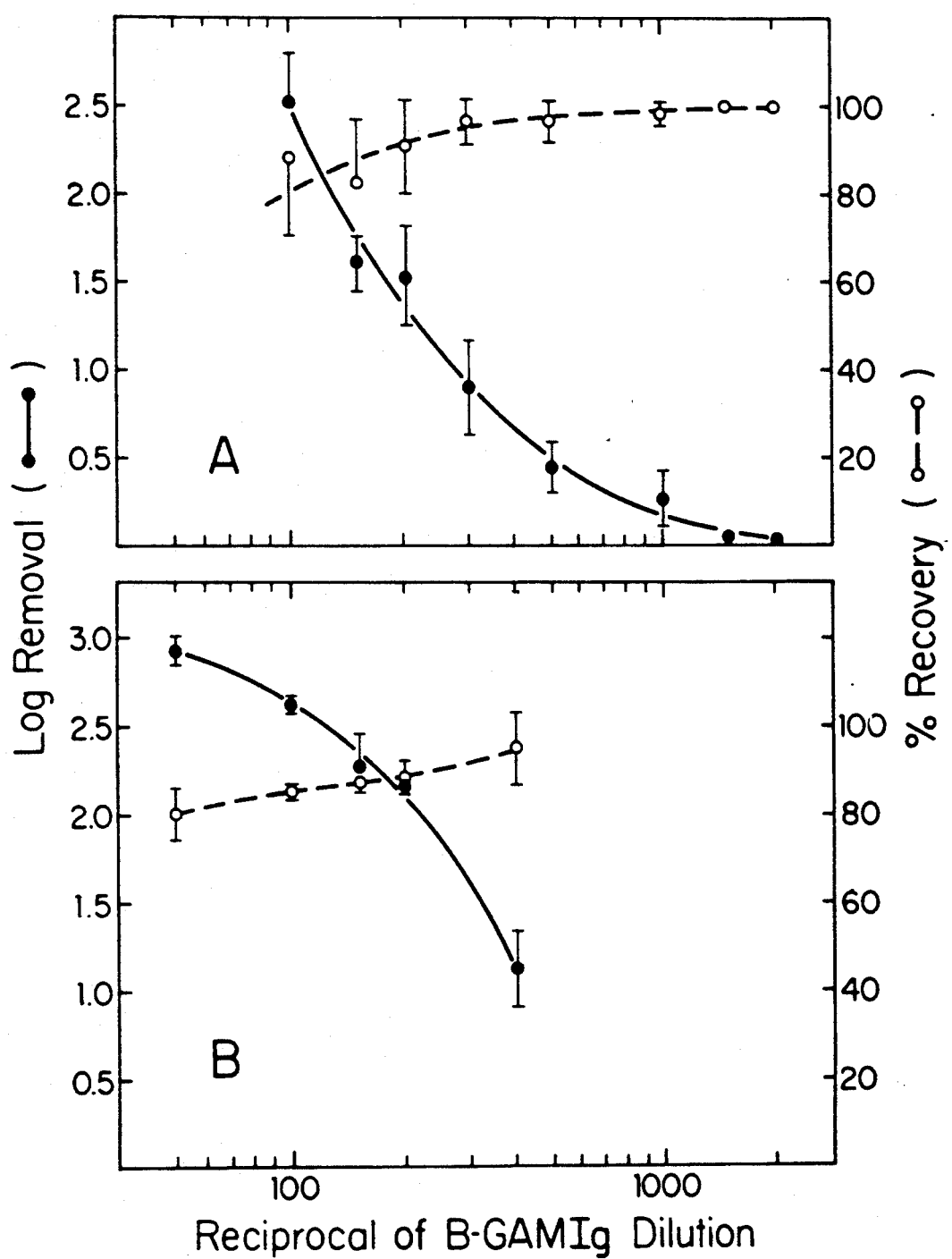
FIG. 4 is a pair of graphs (A and B) showing the effect of biotinylated anti-mouse antibody B-GAMIg on log removal of Daudi cancer cells and percent recovery of noncancerous bone marrow cells after treatment with 10 ug/ml (A) or 30 ug/ml (B) of antibody DM1, as described in Example 11.

Experiments were also performed to study the efficiency of Daudi cell removal when either 10 or 30 ug/ml of antibody DM1 and various dilutions of B-GAMIg were used. Specifically, fifteen million bone marrow cells containing 5-10% Daudi cells were treated successively with 10 ug/ml or 30 ug/ml antibody DM1 and with B-GAMIg at the dilutions indicated on the abscissa of FIG. 4 and then passed over a 3 ml column bed of Sepharose containing 1.0 mg/ml avidin. The results are shown in FIGS. 4A (10 ug/ml antibody DM1) and 4B (30 ug/ml), wherein each data point (except 1:1500 and 1:2000) represents the results of two to four separate experiments. Nearly three logs of Daudi cells were eliminated when the bone marrow and Daudi cell mixture was treated with 30 ug/ml of antibody DM1 followed by 1:50 dilution of B-GAMIg (FIG. 4B). Similar levels of depletion were observed when cells were first treated with 10 or 30 ug/ml of antibody DM1 and then with B-GAMIg at a dilution of 1:100. Daudi cells were less efficiently removed when the dilution of B-GAMIg was increased above 1:100 after treatment with antibody DM1 at 10 ug/ml (FIG. 4A). In contrast, more than two logs of Daudi cells were eliminated using B-GAMIg at a dilution of 1:200 with cells treated with 30 ug/ml of antibody DM1 (FIG. 4B). Marrow recovery was remarkably similar when cells were treated with either 10 ug/ml or 30 ug/ml of antibody DM1. Compared to results with antibody 2H7, Daudi cell depletion after treatment with antibody DM1 appeared to be slightly better at the lower dilutions of B-GAMIg. However, removal of Daudi cells with antibody 2H7 was more than two logs over a wide concentration range of B-GAMIg, while removal of Daudi cells with antibody DM1 was less than two logs when B-GAMIg dilutions greater than 1:200 were used.

Passage of the treated mixture of bone marrow and Daudi cells over columns containing increased amounts of avidin on Sepharose 6MB resulted in more effective depletion of Daudi cells, as shown in TABLE 3. Specifically, fifteen million bone marrow cells containing 5-10% Daudi cells were treated successively with 10 ug/ml antibody DM1 and 1:100 dilution of B-GAMIg and then passed over 3 ml column bed of Sepharose containing the indicated concentrations of avidin. Each avidin concentration was tested in two to four separate experiments.

TABLE 3

| Avidin Concentration (mg/ml) | Log Removal | % Recovery |
| --- | --- | --- |
| 0.5 | 2.41 ± .22 | 85.5 ± 6.6 |
| 0.75 | 2.54 ± .38 | 80.2 ± .07 |
| 1.0 | 2.53 ± .28 | 84.0 ± 13.8 |
| 1.5 | 2.76 ± .26 | 67.9 ± 8.7 |
| 2.0 | 3.05 ± .24 | 69.6 ± 10.6 |

Recovery of bone marrow was decreased when the amount of avidin on the gel was increased. When the cells were treated with a higher dilution of B-GAMIg (1:200), bone marrow recovery was improved to 91.4±10.7% after passage over a 2 mg/ml avidin gel, but depletion of Daudi cells was decreased (2.49±0.02 log removal) compared to results when a 1:100 dilution of this antisera and the 2 mg/ml avidin gel were used (3.05±0.24 log removal and 69.6±10.6% recovery).

EXAMPLE 12

Recovery of hematopoietic progenitors

The growth of hematopoietic progenitors (CFU-C) was assessed after two separate experiments in which 15 million bone marrow cells containing 10% irradiated (1500 Rads) Daudi cells were incubated successively with 10 ug/ml antibody DM1 and 1:100 dilution of B-GAMIg, and then passed over a sterile 3 ml column bed of Sepharose containing 1 mg/ml avidin. Preliminary experiments showed that irradiated Daudi cells did not grow under the conditions utilized for the growth of hematopoietic precursors. As shown in Table 4, preservation of CFU-C was noted in both experiments. Furthermore, nearly quantitative recovery of these hematopoietic progenitors was observed, averaging 96.2±3.3% and 110.7±12.0% in the two experiments. Control experiments showed that the growth of CFU-C was not affected by irradiated Daudi cells (data not shown).

TABLE 4

| Assessment of Effects on Hematopoietic Progenitors (CFU-C) | | | |
| --- | --- | --- | --- |
| Experiment | Pre[a] | Post[a] | Percent Total Recovery[b] |
| 1 | 53.3 ± 10.4 | 79.3 ± 14.6 | 110.7 ± 12.0 |
| 2 | 35.3 ± 2.9 | 42.3 ± 4.0 | 96.2 ± 3.3 |

[a]Number of CFU-C/10[5] cells. The value shown represents the mean of samples that were plated and counted in triplicate. "Pre" indicates the number of CFU-C grown before treatment, while "Post" shows the number of CFU-C after treatment.
[b]Percent Total Recovery indicates the percent recovery of total CFU-C after treatment and was calculated as follows: 100 × [(Post Cell Number)(Post CFU-C)/(Pre Cell Number)(Pre CFU-C)].

DISCUSSION

By incubating a mixture of bone marrow and 5-10% Daudi cells with the biotinylated monoclonal antibody 2H7, which recognizes the Bp32 (CD20) antigen present on Daudi cells, up to two logs of Daudi cells were removed from bone marrow. However, the increased concentrations of avidin on the gel required to achieve highly effective Daudi cell depletion were also associated with decreased recovery of unbound cells. The recovery of unbound cells was not improved by blocking Fc receptors or potential binding sites for biotin on cells with unconjugated, nonreactive antibody or free biotin. Investigators have postulated that biotinylation increases the hydrophobicity of the antibody molecule and that this causes nonspecific binding of biotinylated antibodies on cell surfaces. J. Immunol. Methods 73:83, 1984. However, attempts to decrease the nonspecific loss of bone marrow by decreasing the biotin/antibody conjugation ratio resulted in improved recovery of bone marrow but decreased removal of Daudi cells.

In contrast, as much as three logs of Daudi cells could be removed from bone marrow with the use of the disclosed indirect "sandwich" technique. The use of a biotinylated goat antimouse antiserum eliminates the need to prepare a biotin conjugate of each individual (or type of) specific monoclonal antibody. In comparison to treatment with biotinylated antibody 2H7, the disclosed indirect technique yielded a significant improvement in the recovery of bone marrow. Whereas recovery was reduced below 60% at concentrations of biotinylated antibody 2H7 required to achieve more than two logs of Daudi cell elimination, marrow recoveries up to 90% could be achieved by using dilutions of B-GAMIg that gave a similar degree of Daudi cell depletion. Bone marrow recovery also decreased as the concentration of B-GAMIg was increased. Similar levels of Daudi cell depletion were achieved with either antibody 2H7 or antibody DM1 using B-GAMIg. The slightly improved recovery noted with antibody DM1 compared to antibody 2H7 observed using lower dilutions of B-GAMIg is partly explained by the fact that approximately 4-6% of normal bone marrow cells express Bp32, while only 1-2% of these cells express surface IgM (data not shown).

Depletion was slightly decreased when attempts were made to remove Daudi cells with a combination of antibody 2H7 and B-F(ab')$_2$-GAMIg, although marrow recovery was improved. Dilutions of this biotinylated antiserum as low as 1:10 (70 ug/ml) could not remove more than two logs of Daudi cells. It is possible that differences in the affinity of GAMIg and the F(ab')$_2$ molecule for mouse IgG could explain the findings. A decreased number of biotin conjugation sites on the smaller F(ab')$_2$ fragment could also explain both the decreased specific and nonspecific removal of cells.

Incomplete removal of Daudi cells from bone marrow appears to be primarily due to decreased antigen density on some cells. It has been determined that the Daudi cells remaining after column treatment do not express detectable levels of antigen by immunofluorescence staining (data not shown). These tumor cells may represent a truly antigen negative variant subpopulation or may express amounts of antigen that are below the sensitivity of immunofluorescence studies. Heterogeneity of antigenic expression has also been observed with other tumor cell lines. Immunogenetics 15:385, 1982.

The following Examples demonstrate enrichment of selected lymphoid subpopulations from human and dog bone marrow mononuclear cells and peripheral blood mononuclear cells.

EXAMPLE 13

Positive immunoselection of Ia-positive cells from bone marrow

Thirty to one hundred million dog bone marrow mononuclear cells were obtained as described in Example 5 and then treated with 30 ug/ml of a murine monoclonal antibody (7.2) that specifically reacts with the Ia-antigen. The cell suspension was then reacted with 1:500 dilution of biotinylated goat anti-mouse immunoglobulin B-GAMIg and passed over a 3 ml column bed of Sepharose with 1 mg/ml avidin at a flow rate of 2 ml/min until 10 ml was collected. After washing unadsorbed cells from the column, adherent cells were dislodged from the gel by mechanical agitation with a Pasteur pipette. Following indirect immunofluorescence staining the dislodged cells were analyzed using a fluorescence-activated cell sorter, as described in Example 4. Excellent enrichment of 7.2-positive cells was demonstrated in the adsorbed population. The results are shown in FIG. 5.

Figure 5:
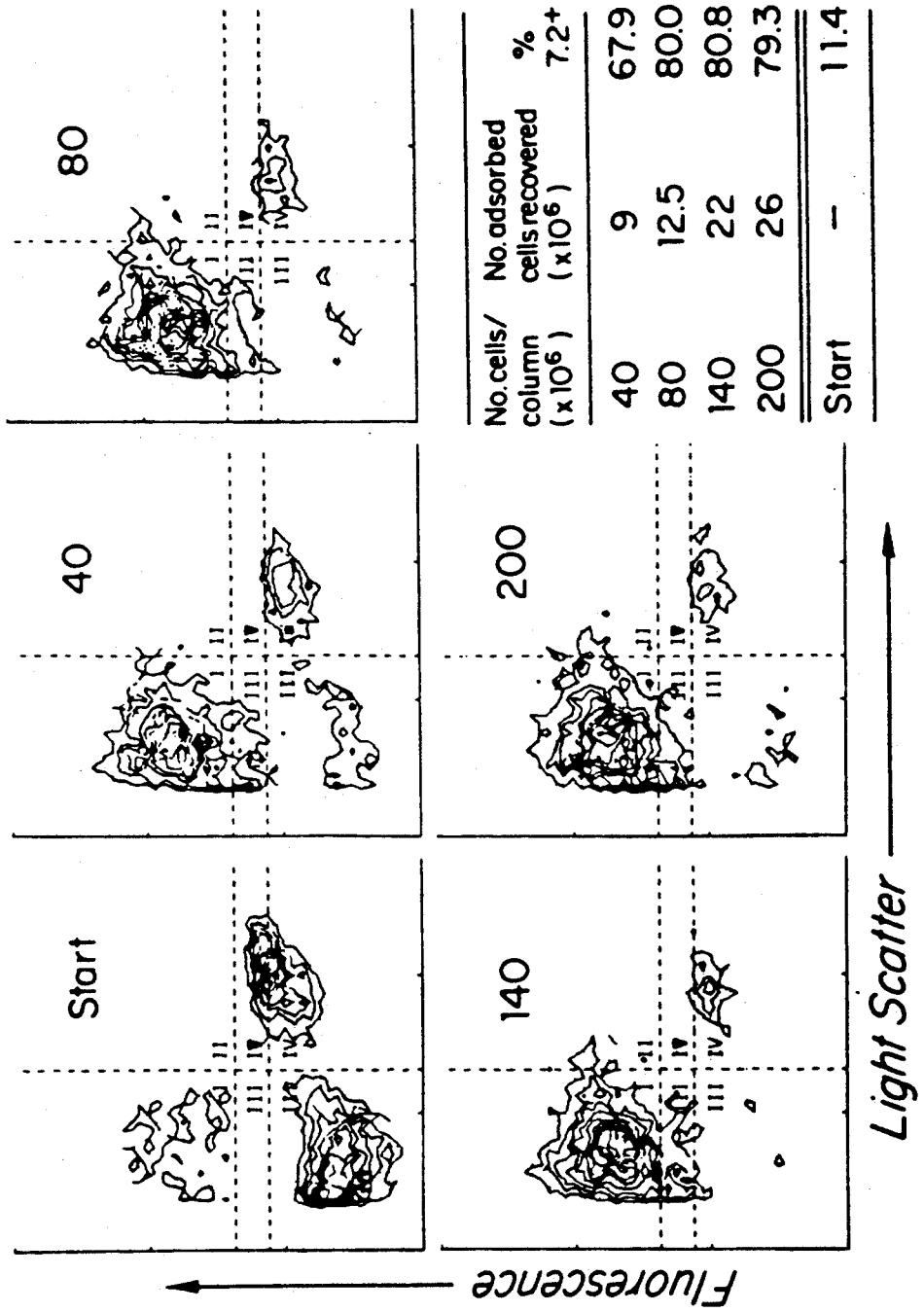
FIG. 5 is a fluorescence-activated cell sorter analysis (five panels) and table demonstrating selective enrichment of an Ia-positive cell population from a suspension of dog bone marrow mononuclear cells, as described in Example 13.

Referring to FIG. 5, the incidences of the Ia-positive cell subpopulation are indicated qualitatively in quadrant I of the five panels, and quantitatively by the density of contour lines within the respective quandrants I. The quantitative results are also summarized in the accompanying table. The five panels show the incidence of Ia-positive cells in the suspension of dog bone marrow mononuclear cells before ("Start") and after column treatment with various numbers of cells: 40, 80, 140, and $200 \times 10^6$ cells per 3 ml column bed of Sepharose with 1 mg/ml avidin. Referring to the table, selective enrichment of Ia-positive cells on the order of 68 to 81 percent were obtained. Both excellent purification and yield were obtained by treating up to $200 \times 10^6$ bone marrow mononuclear cells with this system. Similar results were obtained when treated cells were adsorbed onto avidin-Sepharose or avidin-Biogel. Nonspecific cell binding was limited primarily to cells possessing high forward scatter which light microscopy has shown to be a mixture of granulocytes and monocytes (data not shown).

EXAMPLE 14

Positive immunoselection of T cells from bone marrow

Figure 6:
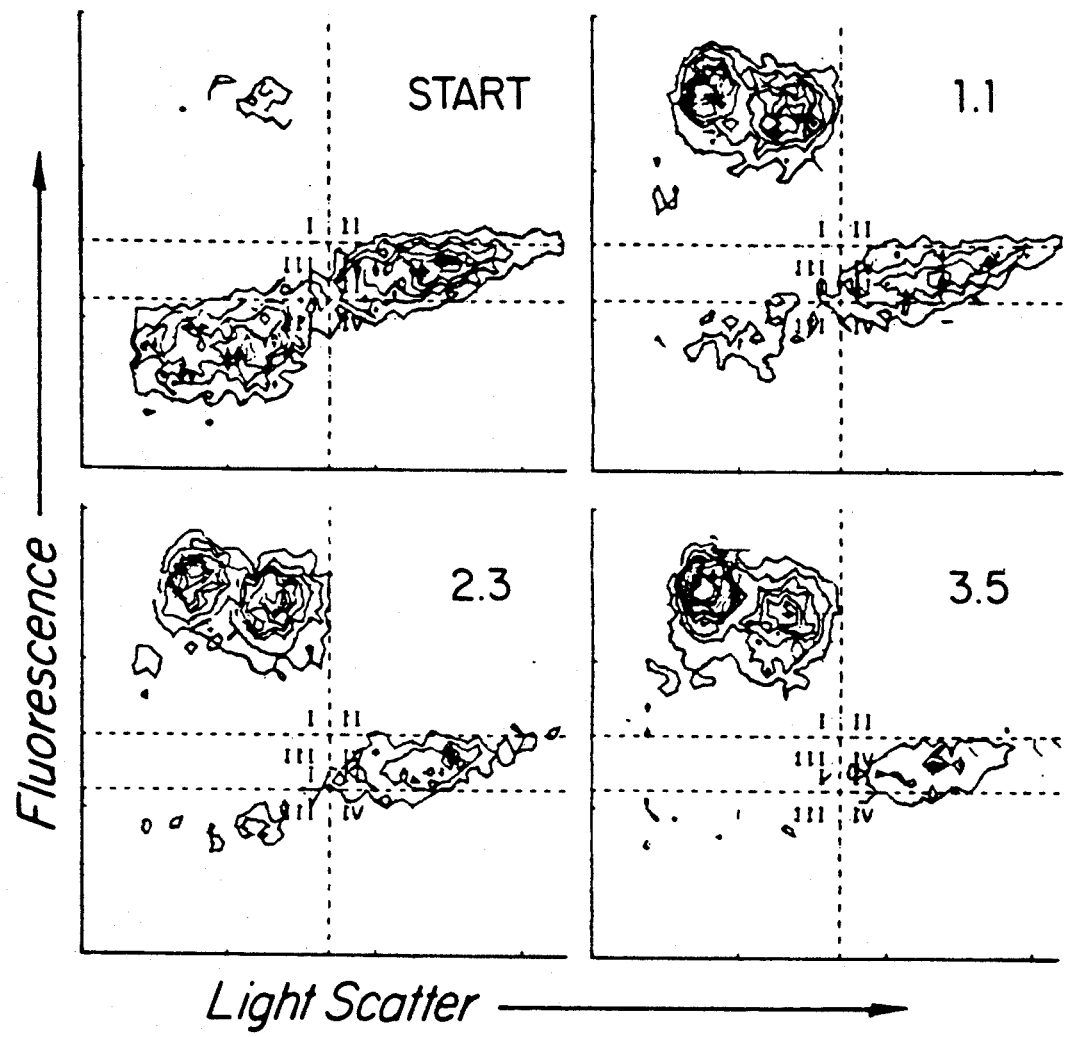
FIG. 6 is a fluorescence-activated cell sorter analysis (four panels) and table demonstrating selective enrichment of a T cell population from a suspension of human bone marrow mononuclear cells, as described in Example 14.

Thirty to one hundred million human bone marrow mononuclear cells were treated successively with 10 ug/ml of a T cell monoclonal antibody (Leu-4; Becton Dickinson) and with 1:500 dilution of biotinylated goat antimouse immunoglobulin B-GAMIg, then passed over a 3 ml column bed of avidin-Sepharose (1 mg/ml avidin) at varying flow rates until a total of 10 ml was collected. Adherent cells were then dislodged by mechanical agitation and stained with avidin-FITC. FIG. 6 shows that the recovered adherent cells became increasingly pure populations of T cells (quadrant I) as the flow rate was increased. Passage of the treated bone marrow mononuclear cells over avidin-Biogel, activated with either glutaraldehyde or carbodiimide, also produced excellent recovery and yield of T-cells (data not shown).

EXAMPLE 15

Proliferative response of positively selected T-cells

Ten thousand bone marrow mononuclear cells suspended in 0.2 ml medium consisting of RPMI with sodium pyruvate, L-glutamine, penicillin, streptomycin, and 15% heat-inactivated pooled human serum were placed in wells of flat-bottomed microtiter plates (Costar, Cambridge, Mass.). Phytohemagglutinin (PHA; Burroughs Wellcome, Research Triangle Park, N.C.) at a final concentration of 1 ug/ml was added to appropriate samples. The plates were then incubated at 37° C. in a 5% $CO_2$ in air incubator for 5 days. Two microcuries of $^3$H-Thymidine (6.7 curies/mmole; New England Nuclear, Boston, Mass.) were added to each well 16 hours before harvesting. Triplicate samples were harvested onto filter paper using a multiple systems-automated harvester (Skatron, Sterling, Va.), placed in scintillation fluid, and counted in a scintillation counter. A stimulation index was calculated by dividing the mean counts per minute (cpm) in PHA-stimulated cultures by the mean cpm of unstimulated cultures.

Adherent human T cells recovered as in Example 14 showed a significantly increased proliferative response to the T cell mitogen (PHA) compared to non-column treated bone marrow mononuclear cells. Additionally, adherent cells recovered after successive treatment with antibody 9E8 (which is not reactive with human or dog tissues including bone marrow and peripheral blood), B-GAMIg, and avidin-Biogel showed virtually no mitogenic response to PHA, which is consistent with FACS data indicating that nonspecifically adherent cells are predominantly composed of granulocytes and monocytes.

EXAMPLE 16

Positive immunoselection of T cells from peripheral blood mononuclear cells

Figure 7:
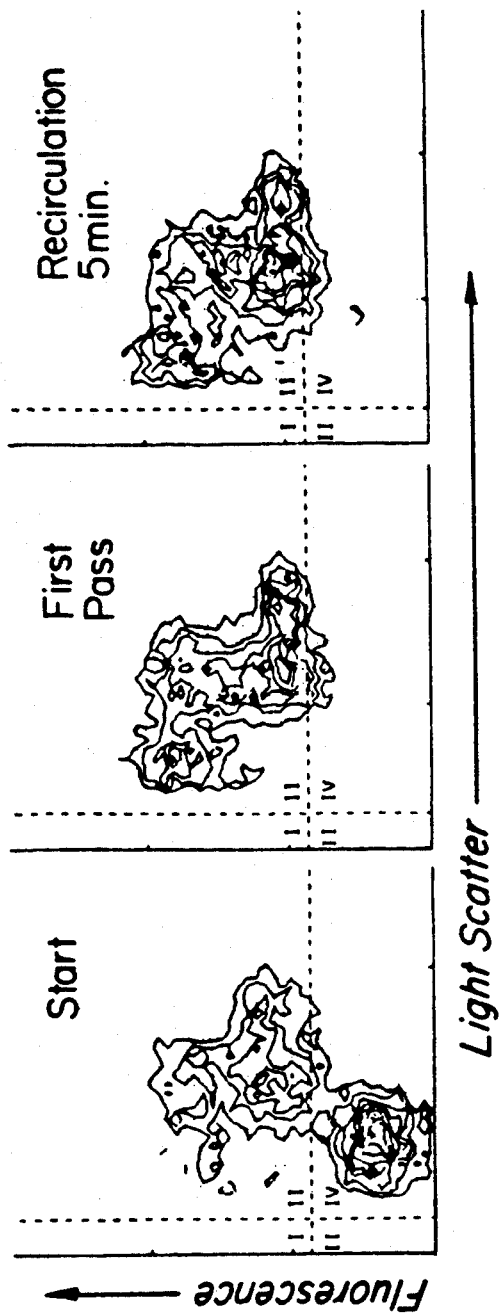
FIG. 7 is a fluorescence-activated cell sorter analysis (three panels) and table demonstrating selective enrichment of a T cell population from a suspension of dog peripheral bone mononuclear cells, as described in Example 16.

Dog peripheral blood mononuclear cells were obtained as described in Example 5 for human bone marrow mononuclear cells. The cell suspension was treated successively with 100 ug/ml of a murine monoclonal antibody (DT2) directed to dog T cells and with 1:500 dilution of biotinylated goat anti-mouse immunoglobulin B-GAMIg. The treated cells were passed over a 3 ml column bed of avidin-Sepharose (1 mg/ml) at a flow rate of 2 ml/min or recirculated for five minutes at a similar flow rate with 10 ml final volume collected. Adherent cells were stained with avidin-FITC and analyzed by fluorescence-activated cell sorter analysis. The results are shown in FIG. 7. Recirculating the cells over avidin-Sepharose for 5 minutes nearly tripled the percent yield of DT-2 positive cells (quadrant II) without significant decrease in purity of the adherent cells.

DISCUSSION

Investigators have previously used avidin-biotin immunoadsorption to bind cells directly to solid phase surfaces, but have experienced difficulties in the recovery of adherent cells due to the tight bond between avidin and biotin. The foregoing Examples demonstrate that the subject immunoselection method can be utilized to not only bind but also recover lymphoid subpopulations from dog and human bone marrow and blood cells, and furthermore that the positively selected cells are viable and functional. Cell viability of recovered adherent cells was judged to be greater than 95% by trypan blue exclusion. Additional studies indicated that recovered T cells were capable of a mitogenic response to the T cell mitogen, phytohemagglutinin (PHA).

Several additional advantages are provided over other cell separation procedures. While the fluorescence activated cell sorter can provide a relatively pure cell population, its limited throughput makes it impractical for sorting more than a few million cells. The "panning" technique in which cells are separated on plastic petri dishes coated with antibodies is simple to use, but produces variable yield and purity of adherent cells, and is cumbersome to use in large scale separation procedures. On the other hand, column immunoaffinity chromatography can be adapted to the separation of several hundred million cells. However, most column procedures rely on the relatively weak binding ($K_D = 10^{-8}$–$10^{-9}$ M) between cell surface antigen and antibody on the solid phase surface and thus require the incubation of cells in the column for attachment of cells to the solid phase surface to occur. Indirect immunoadsorption procedures employing ligands such as protein A, plant lectins, fluorescein isothiocyanate, or goat antimouse immunoglobulin linked to solid phase surfaces also require an incubation period for binding of cells. Our previous experience using columns containing antibodies linked to Sepharose showed that incubation of peripheral blood or bone marrow on a solid phase surface will result in significant nonspecific cell binding. This problem has also been encountered with a variety of matrices including Sepharose, polyacrylamide, silica, and hydroxymethylmethacrylate (data not shown).

In contrast, binding of cells treated with monoclonal antibody and B-GAMIg to avidin-Sepharose or avidin-Biogel was accomplished without incubation, presumably because there is a tremendous affinity between avidin and biotin. Continuous passage of treated cells over these avidin coated surfaces is adequate to bind cells and thus reduces the nonspecific cell binding encountered with other column immunoaffinity procedures. Furthermore, recirculation of dog peripheral blood mononuclear cells successively treated with antibody DT2 and B-GAMIg over avidin-Sepharose markedly increased the yield of DT2-positive cells without a significant decrease in their purity.

The subject cellular immunoaffinity chromatography technique using avidin-biotin can be easily performed in a relatively short period. Reliable and consistent results have been demonstrated with excellent enrichment of a variety of lymphoid populations from peripheral blood and bone marrow. Recovered cells were viable, and positively selected T cells continued to be capable of stimulation by the T cell mitogen PHA. By employing monoclonal antibodies recognizing human pluripotential hematopoietic stem cells, the subject technique is directly applicable to the positive selection of hematopoietic precursors and as such is useful for separating the larger numbers of cells necessary to perform human stem cell transplants. By selecting an appropriate antibody, lymphokine-activated killer cells can be similarly concentrated prior to infusion for tumor therapy.

While the present invention has been described in conjunction with a preferred embodiment, one of ordinary skill after reading the foregoing specification will be able to effect various changes, substitutions of equivalents, and alterations to the subject matter set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A method of immunoselection of target cells comprising the steps of:
    (a) reacting a suspension containing the cells with a first antibody or fragment thereof having binding specificity for the target cells in order to form antibody/cell first complexes;
    (b) reacting the suspension with a biotinylated immunoreagent having specificity for said first antibody or fragment thereof, said immunoreagent being selected from the group consisting of antisera, antibodies or fragments thereof, in order to associate said immunoreagent with said first antibody or fragment thereof to form biotinylated immunoreagent/antibody/cell second complexes;
    (c) reacting the suspension containing the biotinylated second complexes without static incubation with insolubilized avidin contained in a chromatography column or flow-through cartridge in order to associate said avidin with said biotin to form insolubilized avidin/biotinylated immunoreagent/antibody/cell third complexes;
    (d) separating the third complexes from the suspension;
    (e) agitating the third complexes to separate the target cells from the third complexes; and
    (f) recovering viable target cells in substantially enriched form.

2. A kit for removing a specific cell population from a heterogeneous suspension, comprising:
    insolubilized avidin contained in a chromatography column or flow-through cartridge;
    first immunoreagent having binding specificity for said specific cell population; and
    biotinylated second immunoreagent having binding specificity for said first immunoreagent.

* * * * *

UNITED STATES PATENT AND TRADEMARK OFFICE
CERTIFICATE OF CORRECTION

PATENT NO. : 5,225,353

DATED : July 6, 1993

INVENTOR(S) : R. J. Berenson et al.

It is certified that error appears in the above-identified patent and that said Letters Patent is hereby corrected as shown below:

| COLUMN | LINE | |
|---|---|---|
| 1 | 5 | after the title, insert the new paragraph --This invention was made with government support under grants numbers CA18029 and CA26828 awarded by the National Institutes of Health. The government has certain rights in the invention.-- |
| On title page, item [56] "Other Publns." | | "Immunoabsorpton" should read --Immunoabsorption-- |
| On title page, item [56] "Other Publns." | | "Bayer, E.A. t al." should read --Bayer, E.A. et al.-- |
| 2 | 39 | "biotinderivatized" should read --biotin-derivatized-- |
| 3 | 10 | "biotincontaining" should read --biotin-containing-- |
| 7 | 35 | "respresentative" should read --representative-- |
| 10 | 54 | after "EXAMPLE 1" begin a new heading with --<u>Biotinylation of Antibody 2H7</u>-- |
| 13 | 45 | "walls" should read --wells-- |

UNITED STATES PATENT AND TRADEMARK OFFICE
CERTIFICATE OF CORRECTION

PATENT NO. : 5,225,353
DATED : July 6, 1993
INVENTOR(S) : R J. Berenson et al

It is certified that error appears in the above-indentified patent and that said Letters Patent is hereby corrected as shown below:

Column 14, line 22, "concentration" should read --concentrations--

Signed and Sealed this

Twelfth Day of April, 1994

Attest:

BRUCE LEHMAN

*Commissioner of Patents and Trademarks*

*Attesting Officer*